United States Patent

Bon-Lapillonne et al.

Patent Number: 6,007,835
Date of Patent: Dec. 28, 1999

[54] TRANSDERMAL MATRIX SYSTEM

[75] Inventors: Chantal Bon-Lapillonne, Fontaine-lès-Dijon; Daniel Dhuique-Mayer; Claude Mikler, both of Dijon, all of France

[73] Assignee: Laboratoires D'Hygiene Et De Dietetique, Paris, France

[21] Appl. No.: 09/043,726

[22] PCT Filed: Sep. 25, 1996

[86] PCT No.: PCT/FR96/01496

§ 371 Date: Mar. 26, 1998

§ 102(e) Date: Mar. 26, 1998

[87] PCT Pub. No.: WO97/11689

PCT Pub. Date: Apr. 3, 1997

[30] Foreign Application Priority Data

Sep. 27, 1995 [FR] France .................................. 95 11325

[51] Int. Cl.⁶ ............................................................ A61K 9/70
[52] U.S. Cl. .......................................... 424/448; 424/449
[58] Field of Search ..................................... 424/448, 449

[56] References Cited

U.S. PATENT DOCUMENTS

| | | | |
|---|---|---|---|
| 4,655,768 | 4/1987 | Marecki et al. | 424/448 |
| 5,176,916 | 1/1993 | Yamanaka et al. | 424/448 |
| 5,254,348 | 10/1993 | Hoffmann et al. | 424/449 |
| 5,273,757 | 12/1993 | Jaeger et al. | 424/448 |
| 5,411,739 | 5/1995 | Jaeger et al. | 424/448 |
| 5,419,912 | 5/1995 | Morimoto et al. | 424/443 |
| 5,580,572 | 12/1996 | Mikler et al. | 424/448 |

FOREIGN PATENT DOCUMENTS

| | | |
|---|---|---|
| 0285181 | 10/1988 | European Pat. Off. . |
| 0439180 | 7/1991 | European Pat. Off. . |
| 0483370 | 5/1992 | European Pat. Off. . |
| 0674901 | 10/1995 | European Pat. Off. . |
| WO95/18603 | 7/1995 | WIPO . |

*Primary Examiner*—Robert H. Harrison
*Attorney, Agent, or Firm*—Jacobson, Price, Holman & Stern, PLLC

[57] ABSTRACT

A novel transdermal system for the percutaneous delivery of a hormone, including a carrier and an adhesive matrix, is disclosed. The matrix includes (a) 20–50 parts by weight of a poly(styrene-isoprene-styrene) triblock copolymer, (b) 30–60 parts by weight of a tackifyier resin, (c) 4–25 parts by weight of propylene glycol laurate, (d) 2–10 parts by weight of a compound selected from N-alkyl-2-pyrrolidones, wherein the alkyl group is a $C_4$–$C_{15}$ group, (e) 0.01–2 parts by weight of a stabilizing agent, (f) 0.1–12 parts by weight of at least one hormone selected from the group consisting of oestrogenic and progestogenic components, and (g) 1–12 parts by weight of a vinyl acetate/N-vinyl-2-pyrrolidone copolymer. A method for preparing said system and the therapeutical use thereof are also disclosed.

18 Claims, 3 Drawing Sheets

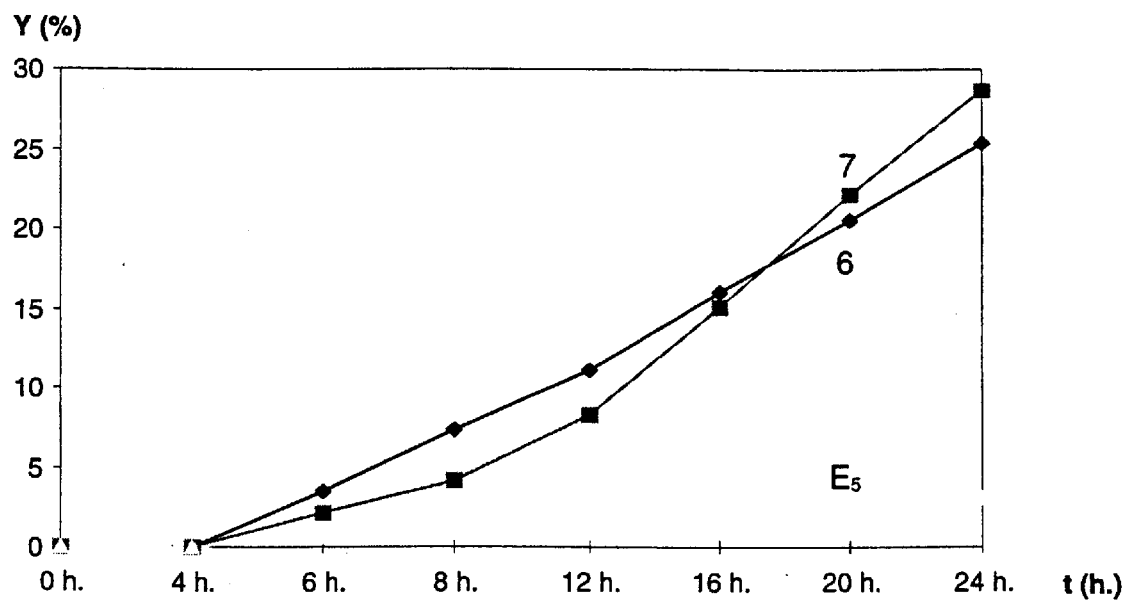

TRANSDERMAL MATRIX SYSTEM

FIELD OF THE INVENTION

The subject of the present invention is a novel transdermal matrix device or system for the prolonged release of an oestrogenic component and/or of a progestogenic component, the said device consisting of a carrier and an adhesive matrix which is composed of a triblock copolymer having A-B-A units of the poly(styrene-isoprene-styrene) [abbreviated to SIS] type and in which there are dissolved the said oestrogenic component and/or the said progestogenic component, propylene glycol laurate combined with a derivative of N-alkyl-2-pyrrolidone and a vinyl acetate/N-vinyl-2-pyrrolidone [abbreviated to VA/VP] copolymer. The invention also relates to a method for preparing the said matrix system and to its therapeutic use.

PRIOR ART

It is known that numerous transdermal systems liberating an oestrogenic component and/or a progestogenic component have already been proposed. Among these, there are so-called "reservoir" systems in which the active ingredient is dissolved a solvent serving as vector for transport across a microporous membrane to the skin. Such is the case of devices based (i) on 17β-oestradiol and (ii) on 17β-oestradiol combined with norethisterone acetate, which are marketed by the company CIBA-GEIGY respectively under the names ESTRADERM® TTS and ESTRAGEST® TTS.

In parallel, so-called matrix systems exist in which the active ingredients are dissolved or dispersed within an adhesive matrix based on polymers such as EVA/acrylic copolymers. This is the case for devices based on 17β-oestradiol which are marketed under the names OESCLIM® and SYSTEN®.

If it is desired to obtain a therapeutically effective final product, it is imperative that all these systems possess a level of delivery of active ingredients for a prolonged period and at a rate sufficient to obtain plasma levels suited to the therapeutic needs.

However, it is known to persons skilled in the art that oestrogenic components and progestogenic components are products which cross the skin barrier with difficulty.

Consequently, the liberated quantities of these active ingredients for obtaining the desired therapeutic effect are in general low compared with the initial quantities present in the transdermal devices, which has as consequence the obtaining of low yields. This causes the use of a quantity of hormone(s) in a large excess relative to that effectively used up.

Likewise, it is known to persons skilled in the art that oestrogenic components and progestogenic components are products which are not very soluble in the polymers used in the so-called matrix transdermal systems.

However, these systems should be relatively small in size and have acceptable adhesion and cohesion properties so as to allow convenient use without impairing clothing by flowing of the mass from the matrix during use. A compromise between an effective rate of transdermal delivery of a hormone, on the one hand, and good physical and ergonomic properties of the systems, on the other, is therefore difficult to achieve and practically impossible in the case of the combined delivery of several hormones. Indeed, in the latter case, the many possible interactions and incompatibilities between the group of components forming the matrix (polymers, resins, solvents, plasticizers, active ingredients, skin absorption enhancers) which should be reconciled with the abovementioned therapeutic dose and physical constraint requirements are multiplied by at least two.

Furthermore, the problem becomes all the more complicated since the hormones exhibit different skin permeabilities and are therefore generally used in different concentrations.

The production of such systems for delivering several hormones rapidly leads to an impasse and very often to products which are not very satisfactory and which are therefore difficult to exploit commercially.

In fact, although, in order to overcome these problems, numerous studies have been carried out using a wide variety of categories of polymers such as EVAs, acrylics, polyisobutenes, silicones and triblock-type copolymers such as poly(styrene-ethylene-butylene-styrene), poly(styrene-butadiene-styrene) and poly(styrene-isoprene-styrene), this undoubtedly explains why no matrix-type product, delivering several hormones simultaneously, is so far commercially available and why the only product commercialized is the ESTRAGEST® TTS system which is of the reservoir type.

Although numerous formulations based on SIS triblock copolymers are already known from EP-A-0 439 180, EP-A-0 285 181 or EP-A-0 483 370, none of these publications discloses or suggests the specific formulations of the invention which make it possible to overcome the problems and disadvantages mentioned above.

AIMS OF THE INVENTION

In the field of the transdermal delivery of an oestrogenic component on its own, of a progestogenic component on its own and in particular of a combination of oestrogenic and progestogenic components, it would be desirable to have available a new technical solution involving a matrix system, and allowing the desired compromise to be made without the abovementioned disadvantages and with, in addition, excellent yields.

According to a first aspect of the invention, it is proposed to provide such a transdermal matrix system, in which the matrix is based on an SIS material, for the delivery of an oestrogenic component and/or of a progestogenic component.

According to a second aspect, it is proposed to provide a method for preparing such a system.

According to yet another aspect of the invention, it is proposed to provide a use of such a matrix system in the treatment of menopause and of osteoporosis.

OBJECT OF THE INVENTION

The abovementioned aims are obtained by virtue of a new technical solution according to the invention which recommends, as novel industrial product, a transdermal matrix system for the percutaneous delivery of at least one hormone, the said matrix system, which comprises a carrier and an adhesive matrix, being characterized in that the said matrix comprises:

(a) 20 to 50 parts by weight of a poly(styrene-isoprene-styrene) triblock copolymer,
(b) 30 to 60 parts by weight of a tackifying resin,
(c) 4 to 25 parts by weight of propylene glycol laurate,
(d) 2 to 10 parts by weight of a compound chosen from N-alkyl-2-pyrrolidones in which the alkyl group is a $C_4$—$C_{15}$ group,
(e) 0.1 to 2 parts by weight of a stabilizing agent,
(f) 0.1 to 12 parts by weight of at least one hormone chosen from the group consisting of oestrogenic components and progestogenic components, (g) 1 to 12 parts by weight of a vinyl acetate/N-vinyl-2-pyrrolidone (VA/VP) copolymer.

According to a second aspect of the invention, there is recommended a method for preparing the said transdermal matrix system, the said method being characterized in that it comprises the following steps which consist either in (α) mixing an SIS polymer, a stabilizing agent and a tackifying resin at a temperature greater than 110° C. and then homogenizing the resulting mixture;

(β) incorporating into the homogeneous mixture thus obtained propylene glycol laurate, an N-alkyl-2-pyrrolidone and a VA/VP copolymer, at a temperature of between 80 and 110° C., and then homogenizing the resulting mixture;

(γ) incorporating into the homogeneous mixture thus obtained at least one hormone chosen from the group consisting of oestrogenic components and progestogenic components, and then homogenizing the resulting mixture;

(δ) coating the homogeneous mixture thus obtained, at a temperature of between 80 and 130° C., onto a temporary anti-adherent carrier so as to obtain a coating of 50 to 300 g/m$^2$ on the said carrier; and, (ε) transferring the said coating onto a permanent carrier; or in (α) introducing, with stirring, into a reactor containing a solvent for an SIS polymer, at a temperature below the boiling temperature of the said solvent, at least one hormone chosen from the group consisting of oestrogenic components and progestogenic components, a stabilizing agent, a VA/VP copolymer, an N-alkyl-2-pyrrolidone and propylene glycol laurate and then homogenizing the resulting mixture;

(β) incorporating into the mixture thus obtained an SIS polymer and a tackifying resin and stirring, still at the same temperature, until complete dissolution of the constituents and complete homogenization of the resulting mixture;

(γ) coating the homogeneous mixture thus obtained, at room temperature, onto a temporary anti-adherent carrier so as to obtain a coating of 50 to 300 g/m$^2$ on the said carrier; and, (δ) evaporating the solvent by heating the said coating at a temperature greater than the boiling point of the said solvent, and then transferring the said coating onto a permanent carrier.

The use of a transdermal matrix system for the production of a medicament intended for a therapeutic use for the symptoms of menopause or osteoporosis is also recommended.

DRAWINGS

In the accompanying drawings, FIGS. 1 to 5 represent the yield (Y), expressed in %, of Es (17β-oestradiol) or NETA (norethisterone acetate) as a function of time (t), expressed in hours.

More precisely, in these drawings,

FIG. 1 makes it possible to compare (in the Y/t system) curves 1, 4 and $E_1$ relating to the yield of 17β-oestradiol release and which are obtained, respectively, with the products of Examples 1 and 4 and a product known by the name ESTRAGEST® TTS and marketed by the company CIBA-GEIGY, on a male "nude" mouse abdominal skin model;

FIG. 2 makes it possible to compare (in the Y/t system) curves 1, 4 and $E_2$ relating to the yield of NETA release and which are obtained, respectively, with the products of Examples 1 and 4 according to the invention and the said ESTRAGEST® TTS, still on a male "nude" mouse abdominal skin model;

FIG. 3 makes it possible to compare (in the Y/t system) curves 1, 3 and $E_3$ relating to the yield of 17β-oestradiol release and which are obtained, respectively, with the products of Examples 1 and 3 according to the invention and a transdermal product known by the name ESTRAGEST® TTS and marketed by the company CIBA-GEIGY on a pig ear skin model;

FIG. 4 makes it possible to compare (in the Y/t system) curves 1, 3 and $E_4$ relating to the yield of NETA release and which are obtained, respectively, with the products of Examples 1 and 3 according to the invention and the said ESTRAGEST® TTS, on a pig ear skin model; and FIG. 5 makes it possible to compare (in the Y/t system) curves 6 and 7 and $E_5$ relating to the yield of 17γ-oestradiol release and which are obtained, respectively, with the products of Examples 6 and 7 according to the invention and a product known by the name OESCLIM® and marketed by the company Laboratoires FOURNIER S.C.A on a male "nude" mouse abdominal skin model.

DETAILED DESCRIPTION OF THE INVENTION

Figure 1:
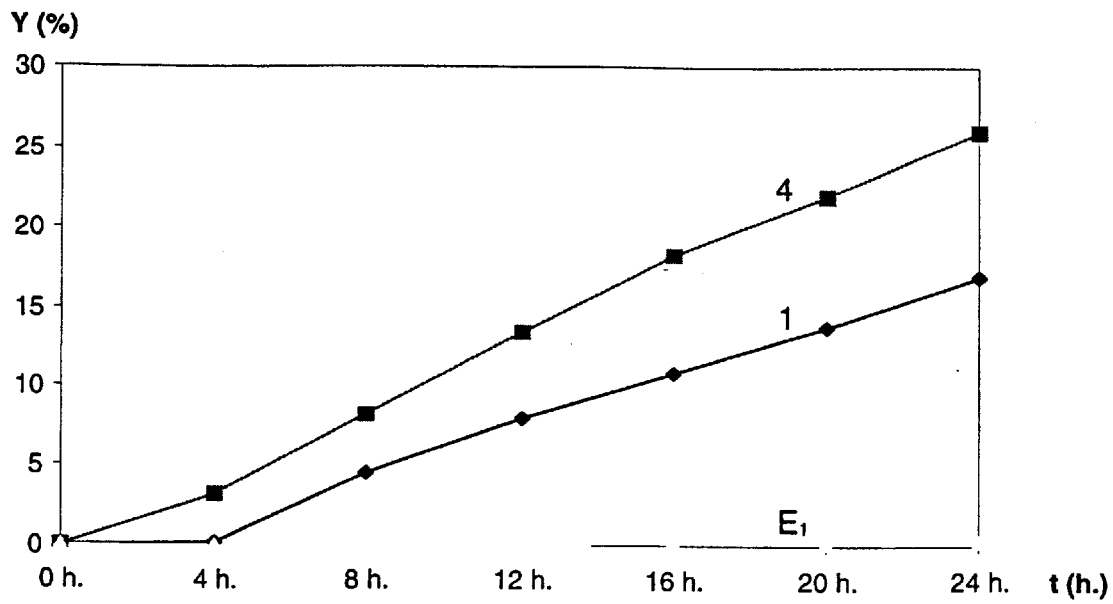

Poly(A-B-A) triblock copolymer of the poly(styrene-isoprene-styrene) [abbreviated to poly(SIS)] type is understood here to mean a poly(SIS) material having a styrene content of between 14 and 50% by weight relative to the weight of the said poly(SIS). Among the products well known to persons skilled in the art, there will be preferably used that marketed by the company DEXCO under the name VECTOR®4211D having a styrene content of 29% by weight relative to the weight of the said poly(SIS) or mixtures of these poly(SIS).

It is also possible to use poly(SIS) containing a mixture of poly(A-B-A) triblock copolymers and poly(A-B) diblock copolymers of the poly(styrene-isoprene) type. Such products, which are well known to persons skilled in the art, are for example marketed by the companies SHELL and EXXON CHEMICAL under the names KRATON®D and VECTOR®4113 or VECTOR®4114 respectively.

Vinyl acetate/N-vinyl-2-pyrrolidone (VA/PV) copolymer is understood here to mean a copolymer having a vinyl acetate content of between 30 and 70% by weight relative to the weight of the said copolymer. Such products are well known for their use as film-forming agents in aerosols and are, for example, marketed under the name "PVP/VA" by the company GAF CORPORATION in the form a powder for the "PVP/VA-S" series, or of a solution in ethanol or isopropanol respectively for the series "PVP/VA-E" and "PVP/VA-I" or by the company BASF under the name Kollidon VA.

There will be preferred in the present invention, in particular, the VA/VP copolymers marketed respectively under the names "PVP/VA-S-630" (which has a content of 40% by weight of vinyl acetate) and Kollidon VA 64 (which has a content of 37.7% by weight of vinyl acetate).

Among the tackifying (or gummy) resins which are suitable according to the invention, there may be mentioned the resins generally used in the field of adhesives by persons skilled in the art, such as polyterpene or modified terpene resins, hydrogenated rosin resins, polymerized rosin resins, rosin ester resins, hydrocarbon resins and the like.

There will be preferred in particular the hydrocarbon resins such as those marketed by the company EXXON CHEMICAL under the name ESCOREZ® (such as the resins ECR®385, ECR®179A and ECR®179C). These resins make it possible, indeed, in combination with the preferred SIS according to the invention, to obtain optimum adhesive properties. "Active ingredient" or "hormone" is understood here to mean any oestrogenic component, any progestogenic component or any oestrogenic component/progestogenic component mixture which can be used by the transdermal route.

Among the oestrogenic components which are suitable according to the invention, there may be mentioned in particular 17β-oestradiol and the oestradiol derivatives, in particular the mono- and diesters of oestradiol, such as for example oestradiol 17-acetate, oestradiol 3,17-diacetate, oestradiol 3-benzoate, oestradiol 17-undecanoate, the derivatives alkylated at the 17 position of oestradiol such as ethinyloestradiol, ethinyloestradiol 3-isopropyl sulphonate, methyloestradiol, quinestrol, mestranol and, where appropriate, mixtures thereof.

Among the progestogenic components which are suitable according to the invention, there may be mentioned in particular progesterone, medrogesterone and derivatives thereof (in particular 17-hydroxyprogesterone acetate, medroxyprogesterone acetate), norethisterone and its derivatives, in particular 17-norethisterone acetate, levonorgestrel and nomegestrol acetate.

According to the present invention, there will be preferably used as oestrogenic component 17β-oestradiol (Es) and as progestogenic component norethisterone acetate (NETA). The transdermal matrix system according to the invention may in particular contain simultaneously an oestrogenic component and a progestogenic component.

Among the stabilizing agents used according to the invention there may be mentioned the antioxidants commonly used by persons skilled in the art, such as for example the products marketed by the company CIBA-GEIGY under the name IRGANOX® such as IRGANOX®565.

Propylene glycol laurate is understood here to mean an ester of lauric acid and of propylene glycol, that is to say a monoester, a diester or a mixture of mono- and diester of propylene glycol ($CH_3$—CHOH—$CH_2$—OH) and of lauric acid ($C_{12}H_{24}O_2$). There will be preferred in particular a mixture of mono- and diester such as the product marketed under the name LAUROGLYCOL® by the company GATTEFOSSE.

Among the N-alkyl-2-pyrrolidones, where the alkyl group is a $C_4$—$C_{15}$ group, which are used in the present invention, N-octyl-2-pyrrolidone marketed by the company GAF CORPORATION under the name SURFADONE® LP 100 will be preferred.

The carrier receiving the matrix may be any carrier generally used in occlusive or nonocclusive transdermal systems, of variable thickness and impermeable to the constituents of the matrix. There will be preferred, for example, a carrier in the form of a film made from polyethylene, polypropylene, polyester, a complex (or composite) consisting of polyethylene or a vinyl acetate/ethylene copolymer, or alternatively foams. If necessary, an additional, for example peripheral, adhesive band may be added to the device in order to optimize its skin adhering properties. This adhesive band, which describes a ring around the matrix system, consists of a pressure-sensitive adhesive well known to persons skilled in the art, such as for example a pressure-sensitive adhesive based on an acrylic copolymer.

In practice, the surface of the matrix which is not linked to the carrier may be coated with a protective layer or film which can be peeled off before using the device. The said device itself may be packaged in a sealed protection such as for example polyethylene-aluminium complexes.

By virtue of the specificity of the composition of the formulations which can form the matrix, only the matrix system according to the invention has the numerous advantages which will now be disclosed.

It has indeed been found that only the composition defined above, containing (1) the pair (i) propylene glycol laurate and (ii) a compound chosen from N-alkyl-2-pyrrolidones where the alkyl group is a $C_4$—$C_{15}$ group, (2) an SIS material, and (3) a VA/VP copolymer, makes it possible to obtain a matrix system for delivering one or, in particular more hormones, which exhibits the desired ergonomic and therapeutic properties and which makes it possible to obtain remarkable yields.

This can undoubtedly be explained by (i) a specific synergistic effect between the nature of the poly(styrene-isoprene-styrene) triblock copolymers which tend to "push" the hormone(s) present which are hardly soluble in them, and (ii) the specific propylene glycol laurate plasticizer role which will separate the polymeric SIS chains, allowing them greater movements, and thus reduce the rigidity of the macromolecular network, thereby facilitating overall the circulation of the hormone(s).

However, this plasticizing compound, which is a derivative of a fatty substance, can, if used in an excessively large quantity, alter the adhesive and/or cohesive properties of the matrix. Accordingly, it is essential that it be combined with an enhancer of skin permeation which is different in nature, such as an N-alkyl-2-pyrrolidone, so as to obtain the desired delivery levels and to achieve a better yield without substantial loss of adhesion or cohesion.

Finally, the use of the VA/VP copolymer makes it possible to enhance the solubility of the hormones which are used in the matrix. Furthermore, surprisingly, although this VA/VP copolymer is used in the adhesive masses because it makes it possible to enhance the adhesion of the matrix and therefore contact with the skin, it also causes a substantial reduction in skin irritation which may be due to a mechanical effect of the system or to the combined effect of the group of compounds or to the effect of one specific compound such as a skin permeation enhancer.

Furthermore, by virtue of the possibility of using less oestrogenic component and/or progestogenic component while obtaining larger delivered quantities, the development and the production of the formulations forming the matrix of the devices are simplified.

The problems of the solubility of the hormones in the SIS copolymers as well as the risks of physical incompatibility with the other constitutents of the matrix are thus minimized or eliminated.

By virtue of all these synergistic effects, the production of acceptable and reliable, and therefore marketable, matrix systems for the administration of two hormones becomes possible.

Finally, the obtaining of yields respectively at 24 hours and 48 hours of oestrogenic component of the order of 20 to 50% and/or of progestogenic component of the order of 10 to 14% according to the skin models used, leads to very competitive systems. Indeed, a final non-negligible advantage is that of the cost price, which is quite substantially reduced compared with known prior art devices, by virtue of the use of a small quantity of hormone whose price is high.

The transdermal matrix systems according to the invention are produced based on the techniques generally used by persons skilled in the art: either by coating (in the solvent phase), or according to the so-called "hot-melt" technique (that is to say in the absence of solvent). In both cases, in the context of an industrial production, large areas are coated and then cut to give devices of the appropriate sizes, according to the quantity of hormone(s) present per unit of surface area, at the chosen dose of active ingredient to be delivered over a given time.

In the case of the so-called solvent phase technique, there is recommended a method for preparing an adhesive transdermal matrix system according to the invention which comprises the following steps:

(1) the active ingredient(s), the VA/VP copolymer, the stabilizer, the N-alkyl-2-pyrrolidone and the propylene glycol laurate are introduced, while heating at a temperature below the boiling point of the solvent (for example 50 to 60° C. in the case of ethyl acetate), into a thermostatted reactor containing a solvent for the SIS polymer, and the mixture is stirred until it is homogenized;

(2) the tackifying resin and the SIS copolymer are incorporated into the mixture obtained in step (1), still with stirring, while heating at the same temperature, and the mixture is homogenized until the constituents are completely dissolved;

(3) the homogeneous mixture thus obtained in step (2) is coated, at room temperature, onto a nonadherent temporary carrier, for example a silicone polyester film, at the rate of 50 to 300 g/m$^2$;

(4) the coating is heated in order to evaporate the solvent at a temperature, depending on its boiling point, of between 40 and 110° C., and preferably at a temperature of 60 to 80° C.; and, (5) the resulting dry matrix is transferred onto the final carrier chosen.

In the case of the "hot-melt" technique, a method is recommended which comprises the following steps:

(1a) in a mixer, the tackifying resin is incorporated into the SIS polymer/stabilizing combination, with stirring, at a temperature greater than 110° C., preferably at a temperature of 180° C., in successive portions of 10%, 30% and 60%, such that for each portion, a perfectly homogenous mixture is obtained;

(2a) the propylene glycol laurate, the N-alkyl-2-pyrrolidone and the VA/VP copolymer are then gradually incorporated into the mixture obtained in step (1a), still with stirring and at generally lower temperatures than in step (1a) which are determined by the heat-stability of these products; the resulting mixture is again stirred until it is completely homogenized;

(3a) the active ingredient(s) is(are) incorporated into the homogeneous mixture thus obtained in step (2a), at a temperature of the order of 100° C., and the mixture is further stirred until a perfectly homogeneous mixture is obtained;

(4a) the homogeneous mixture thus obtained is coated, at a temperature of between 80 and 130° C., onto a nonadherent temporary carrier, in particular a silicone polyester film, so as to obtain a deposit of 50 to 300 g/m$^2$; and, (5a) the matrix thus obtained in step (4a) is transferred onto the final carrier chosen.

The transdermal systems according to the invention are in particular useful for the treatment of the symptoms of menopause and of the ensuing cardiovascular risks, osteoporosis as well as for any therapy using the percutaneous route requiring the delivery of oestrogens and/or progestogens.

BEST MODE

The best mode of carrying out the invention consists in using a transdermal matrix system whose matrix contains, for a total of 100 parts by weight:

(a) 34.3 parts by weight of SIS,
(b) 41 parts by weight of a tackifying resin,
(c) 14 parts by weight of propylene glycol laurate,
(d) 4 parts by weight of N-octyl-2-pyrrolidone,
(e) 0.2 part by weight of a stabilizing agent,
(f$_1$) 0.5 part by weight of 17β-oestradiol,
(f$_2$) 3 parts by weight of norethisterone acetate,
(g) 3 parts by weight of a vinyl acetate/N-vinyl-2-pyrrolidone (VA/VP) copolymer,
on the one hand, or
(a) 37.8 parts by weight of SIS,
(b) 38 parts by weight of a tackifying resin,
(c) 15 parts by weight of propylene glycol laurate,
(d) 4 parts by weight of N-octyl-2-pyrrolidone,
(e) 0.2 part by weight of a stabilizing agent,
(f) 1 part by weight of 17β-oestradiol,
(g) 4 parts by weight of a vinyl acetate/N-vinyl-2-pyrrolidone (VA/VP) copolymer,
on the other hand, or
(a) 31.3 parts by weight of SIS,
(b) 44 parts by weight of a tackifying resin,
(c) 10.5 parts by weight of propylene glycol laurate,
(d) 4 parts by weight of N-octyl-2-pyrrolidone,
(e) 0.2 part by weight of a stabilizing agent,
(f) 4 parts by weight of norethisterone acetate,
(g) 6 parts by weight of a vinyl acetate/N-vinyl-2-pyrrolidone (VA/VP) copolymer.

In these formulations, the SIS used advantageously has a styrene content of between 14 and 50% by weight relative to the weight of the said poly(SIS). The VA/VP copolymer, for its part, advantageously has a vinyl acetate content of between 30 and 70% by weight relative to the weight of the said VA/VP.

Other advantages and characteristics of the invention will be understood more clearly on reading the following description of exemplary embodiments and of comparative tests on the products currently commercialized.

Of course, all these elements are not at all limiting but are given by way of illustration.

For convenience, the following abbreviations have been used in the text which follows:
NETA: norethisterone acetate
SIS: poly(styrene-isoprene-styrene) triblock copolymer
VA/VP: vinyl acetate/N-vinyl-2-pyrrolidone copolymer
Es: 17β-oestradiol

EXAMPLE 1

Into a 250 ml beaker, there are successively introduced 0.25 g of 17β-oestradiol, 1 g of NETA, 3 g of PVP/VA-S-630 (vinyl acetate/N-vinyl-2-pyrrolidone copolymer having a content of 40% by weight of vinyl acetate units and marketed by the company GAF CORPORATION), 0.1 g of IRGANOX®565 (antioxidant marketed by the company CIBA-GEIGY), 2 g of SURFADONE® LP 100 (N-octyl-2-pyrrolidone marketed by the company GAF CORPORATION), 6 g of LAUROGLYCOL® (mixture of mono- and diester of propylene glycol and of lauric acid marketed by the company GATTEFOSSE) and 30 g of ethyl acetate.

This mixture is stirred while heating at 50° C. for about 15 minutes. 19 g of ECR®385 (tackifying resin marketed by the company EXXON CHEMICAL) and 18.65 g of VECTOR®4411 D (SIS copolymer marketed by the company EXXON CHEMICAL) are then incorporated and the mixture is stirred at 50° C. until complete dissolution of the compounds is obtained.

The mixture obtained is then coated onto a film of silicone polyester at the rate of (100±10) g/m$^2$ at room temperature (15–25° C.). The coating thus produced is heated at 50° C. for at least 30 minutes in order to evaporate the solvent and then transferred onto a final carrier made of nonsilicone polyester.

Shapes of the appropriate sizes are then cut and packaged in heat-sealable bags.

EXAMPLE 2

The procedure is carried out in the same manner as in Example 1, but using in this case 5.5 g of LAUROGLYCOL® and 1.5 g of NETA.

EXAMPLE 3

The procedure is carried out in the same manner as in Example 1, but using in this case 0.25 g of 17β-oestradiol, 1.5 g of NETA, 1.5 g of PVP/VA-S-630, 0.1 g of IRGANOX®565, 2 g of SURFADONE® LP 100, 7 g of LAUROGLYCOL®, 30 g of ethyl acetate, 20.5 g of ECR®385 and 17.15 g of VECTOR®4411 D and the coating is carried out in this case at the rate of (80±10) g/m².

EXAMPLE 4

The procedure is carried out in the same manner as in Example 1, but using in this case 0.25 g of 17β-oestradiol, 1 g of NETA, 1.5 g of PVP/VA-S-630, 0.1 g of IRGANOX®565, 2 g of SURFADONE® LP 100, 7.5 g of LAUROGLYCOL®, 30 g of ethyl acetate, 20.5 g of ECR®385 and 17.15 g of VECTOR®4411 D.

EXAMPLE 5

The procedure is carried out in the same manner as in Example 4 with the difference that in the present case the coating is carried out at the rate of (75±10) g/m².

EXAMPLE 6

The procedure is carried out according to the protocol described in Example 1 but without NETA. 0.5 g of 17β-oestradiol, 2 g of PVP/VA S-630, 0.1 g of IRGANOX®565, g of SURFADONE® LP 100, 7.5 g of LAUROGLYCOL®, 30 g of ethyl acetate, 19 g of ECR®385 and 18.9 g of VECTOR®4411 D are incorporated.

EXAMPLE 7

The procedure is carried out in the same manner as in Example 6 but using in this case 0.5 g of 17β-oestradiol, 1 g of PVP/VA S-630, 0.1 g of IRGANOX®565, 2 g of SURFADONE® LP 100, 7.5 g of LAUROGLYCOL®, 30 g of ethyl acetate, 21 g of ECR®385 and 17.9 g of VECTOR®4411 D.

EXAMPLE 8

The procedure is carried out according to the protocol described in Example 1 but without 17β-oestradiol. 2 g of NETA, 3 g of PVP/VA S-630, 0.1 g of IRGANOX®565, 2 g of SURFADONE® LP 100, 5.25 g of LAUROGLYCOL®, 30 g of ethyl acetate, 22 g of ECR®385 and 15.65 g of VECTOR®4211 D, (SIS copolymer marketed by the company DEXCO) are incorporated in this case.

EXAMPLE 9

The procedure is carried out in the same manner as in Example 8 but using in this case 1.5 g of NETA, 1.5 g of PVP/VA S-630, 0.1 g of IRGANOX®565, 2 g of SURFA-DONE® LP 100, 7.25 g of LAUROGLYCOL®, 30 g of ethyl acetate, 22 g of ECR®385 and 15.65 g of VECTOR®4211 D.

Tests

Figure 2:
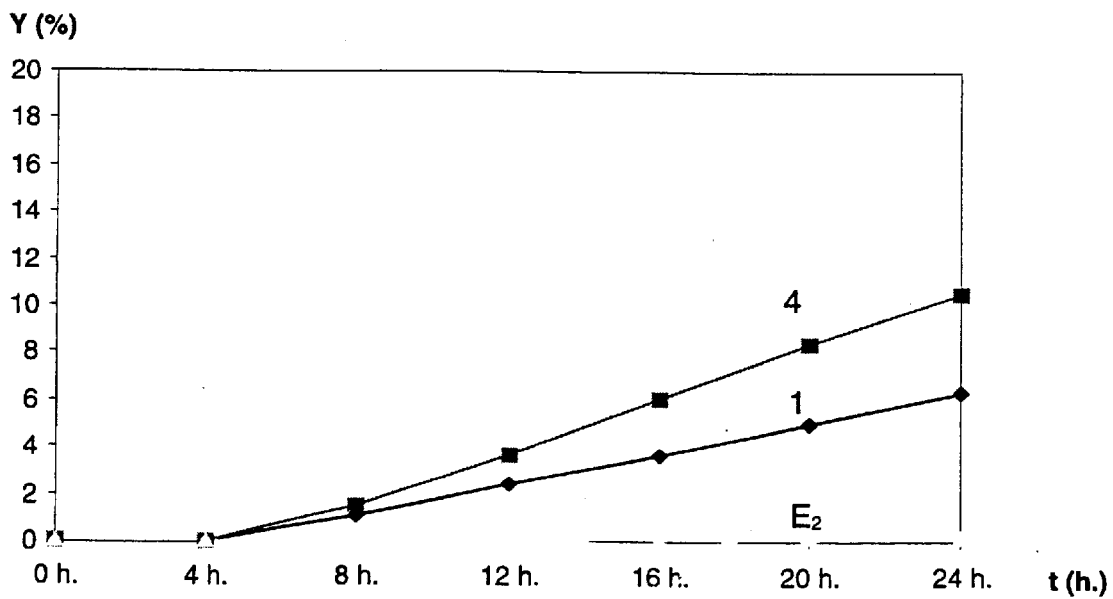
Figure 3:
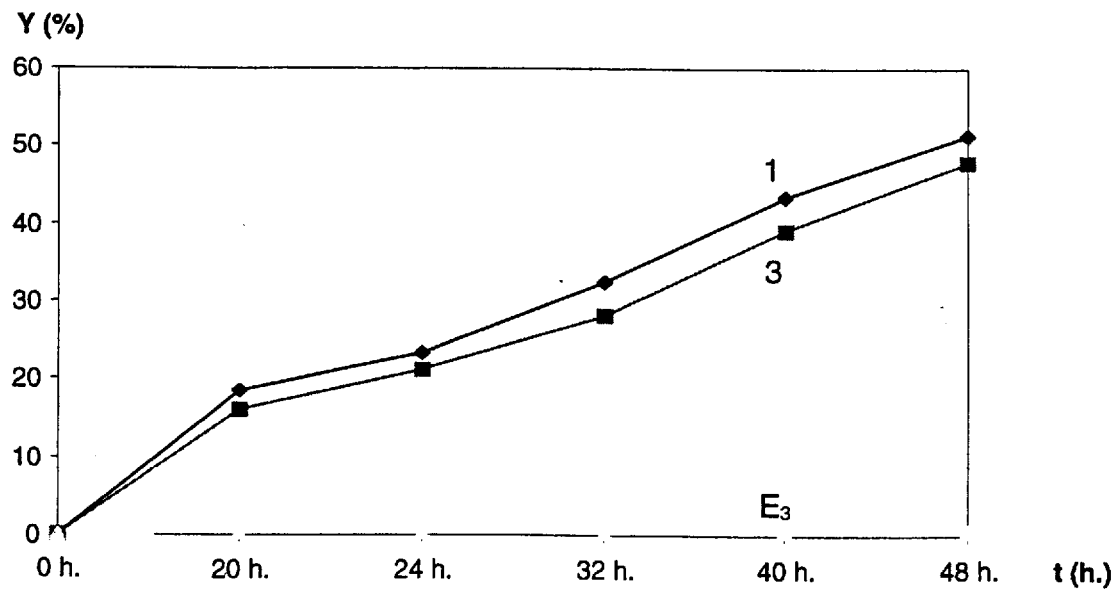
Figure 4:
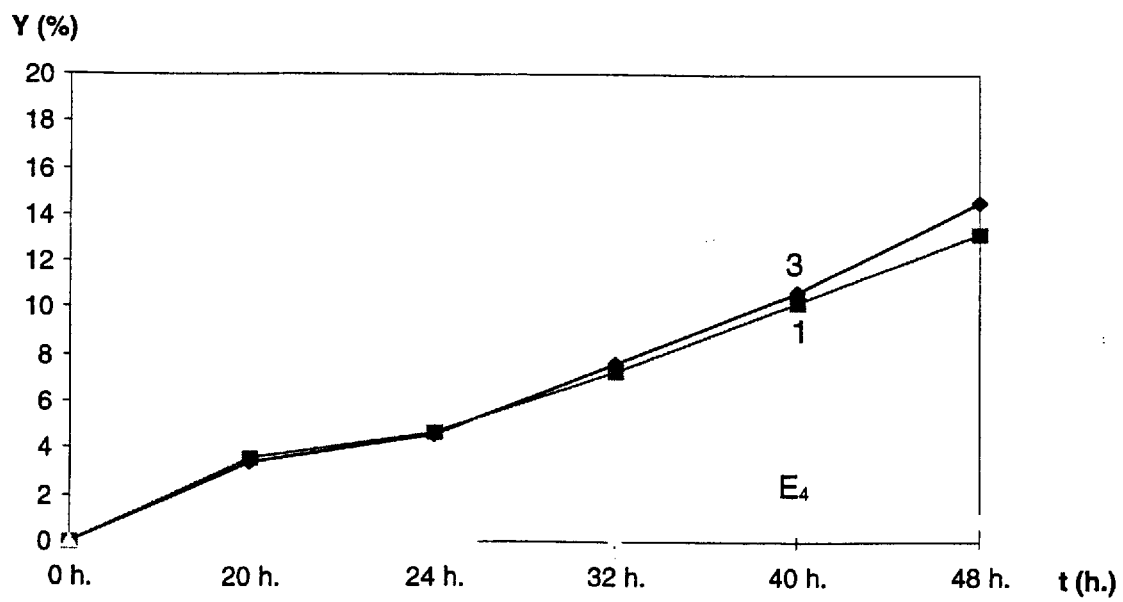

Some of the results obtained in the context of the comparative tests were grouped together in FIGS. 1 to 5 and Tables I to V.

Measurements ex vivo were thus carried out, using the devices described in the examples given above, of quantities of hormone(s) liberated over 24 hours or 48 hours on various skin models and the corresponding yields calculated. Comparison with other systems already known clearly illustrates the advantages of the devices according to the invention.

For that, tests of permeation were carried out ex vivo on male "nude" mouse abdominal skin according to the following protocol.

The measurement of the quantities of hormone(s) liberated by a transdermal device with a surface area of 2.54 cm² previously cut out with a punch and deposited on a disc of 3.14 cm² of male "nude" mouse abdominal skin is carried out by means of a static glass cell thermostatted at 37° C. and having a receiving compartment with a volume of 11.5 ml containing, as recipient phase, a physiological saline/PEG 400 (72/25 v/v) mixture.

The samples are collected from the receiving compartments at 2, 4, 6, 8, 12, 16, 20 and 24 hours and assayed by liquid chromatography.

Given the variability of the results linked to the intrinsic permeability of the skin samples, each test of permeation for a sample of transdermal device is carried out on a minimum number of 3 to 5 skin samples. A result which is the mean for each device, obtained from these tests, is given here.

The ratio of this mean value of the quantities of hormone (s) liberated at the end of the kinetics over 24 hours to the initial quantity of hormone(s) contained in the device makes it possible to evaluate the yield, over 24 hours, of the transdermal systems according to the invention.

Comparative measurements were thus carried out for the only known system currently marketed and which contains both an oestrogen and a progestogen, namely the product ESTRAGEST® TTS from the company CIBA-GEIGY. This product is also the only one currently available commercially which contains a progestogen although the latter is in combination with 17β-oestradiol.

In the case of the product ESTRAGEST® TTS, the device consists of two adjoining reservoirs containing in total 10 mg of 17β-oestradiol and 30 mg of NETA, each reservoir containing a mixture of 5 mg of 17β-oestradiol and 15 mg of NETA. The measurements of skin permeation are then carried out according to the same protocol on only one of the two reservoirs placed on a skin sample of 3.14 cm².

The initial quantities of each hormone contained in this reservoir are expressed in terms of the quantity of the said hormone per unit surface area expressed in µg/cm².

In one reservoir, there is found on average an initial hormone value per unit surface area of 1570 µg/cm² of Es and of 4790 µg/cm² of NETA.

Likewise, the ratio of, respectively, (i) the value of the quantities of Es or of NETA liberated over 24 hours to (ii) the initial quantities contained in the reservoir, makes it possible to obtain the yields, over 24 hours, of Es and NETA.

The matrix systems according to the invention, containing Es and NETA, were thus compared to the known transdermal system ESTRAGEST® TTS mentioned above. The results obtained have been collated in Table I below.

In a second step, comparative measurements were also carried out ex vivo on another skin model, pig ear skin, still relative to the said ESTRAGEST® TTS.

The operating protocol for these measurements is identical to that for the measurements ex vivo on "nude" mouse abdominal skin. This time a disc of 3.14 cm² of pig ear skin is available. The recipient phase is in this case a physiological saline/PEG 400/ethanol (66/18/16, v/v/v) mixture. On the other hand, samples were collected here for 48 hours.

The result obtained is still the mean obtained for each device tested on a minimum number of 3 to 5 samples of skin.

The ratio of (i) this mean value of the quantity of hormone liberated at the end of the kinetics over 48 hours, (ii) the initial quantity of hormone contained in the device, makes it possible to evaluate the yield, over 48 hours, of the transdermal systems.

The corresponding results have been collated in Table II.

Tests of permeation were also carried out on a human skin dermatomic at 700 μm, stored in a desiccator for 10 to 30 days and then rehydrated just before use in a phosphate buffer at pH 7.4. The same operating protocol is applied as for the tests on pig skin. The recipient phase is in this case a physiological saline/PEG 400/ethanol (66/18/16, v/v/v) mixture. The samples are collected over a period of 48 hours.

Table III presents the results of the tests of skin permeation ex vivo on human skin for the devices of Examples 3 and 5 and the product ESTRAGEST® TTS.

Moreover, the yields obtained for devices according to the invention and a commercial matrix device containing a single hormone were compared. In the present case, the measurements were carried out with the product OESCLIM® and devices according to the invention both of which contain 17β-oestradiol alone.

For that, tests of permeation were carried out ex vivo, still according to the same protocol, on male "nude" mouse abdominal skin with the aid of samples of 2.54 cm² of OESCLIM®. With this device, there are found on average an initial value of 17β-oestradiol per unit surface area of 452 βg/cm² and a quantity of 17β-oestradiol liberated over 24 hours on this skin model of 14.2 μg/cm².

Table IV presents the calculated yields, for Examples 6 and 7, of the devices according to the invention and the product OESCLIM®.

Finally, the yields obtained for two devices (Examples 8 and 9) according to the invention, containing a single hormone NETA, and the transdermal system ESTRAGEST® TTS cited above were compared.

For that, tests of permeation were carried out, still according to the same protocol as that described in order to obtain the results of Table I, ex vivo on male "nude" mouse abdominal skin. All the results obtained are assembled in Table V.

Analysis of Table I shows that, in all cases, both for Es and for NETA, yields are obtained which are substantially higher than those for the device ESTRAGEST® of the order of 130-fold for Es and 65-fold for NETA in the best cases.

There are obtained, respectively, for Es:

a yield 84-fold higher for Example 1, a yield 112-fold higher for Example 2, a yield 133-fold higher for Example 3, and a yield 130-fold higher for Example 4.

Likewise, there are obtained for NETA:

a yield 37-fold higher for Example 1, a yield 29-fold higher for Example 2, a yield 65-fold higher for Example 3, and a yield 62-fold higher for Example 4.

Analysis of Table II, this time on studies carried out on pig ear skin, confirms, also with this skin model, these excellent results.

There are obtained, respectively, for Es:

a yield 84-fold higher for Example 1, a yield 64-fold higher for Example 2, a yield 78-fold higher for Example 3, and a yield 66-fold higher for Example 4.

Likewise, there are obtained for NETA:

a yield 15-fold higher for Example 1, a yield 11-fold higher for Example 2, a yield 16-fold higher for Example 3, and a yield 11-fold higher for Example 4.

Analysis of Table III, which groups together the results obtained based on the studies carried out on human skin, demonstrates, on a model even closer to reality, the indisputable advantage of the product according to the invention in relation to the only system for delivering 2 hormones which is currently marketed.

There are indeed observed, respectively, yields 120-fold and 144-fold higher for Examples 3 and 5 in the case of Es and 100- and 125-fold higher in the case of NETA relative to the product ESTRAGEST® TTS.

Analysis of Table IV shows, if a system containing only 17β-oestradiol is considered, that the systems according to the invention are also, from the point of view of the yields, quite superior to a product containing an oestrogen alone, for example the product OESCLIM®. There are thus obtained, respectively, relative to OESCLIM®, a yield 8.2-fold and 9.3-fold higher for Examples 6 and 7.

If the case of the administration of a single hormone is considered, the devices according to the invention are therefore still equally efficient.

Likewise, analysis of Table V shows, if a system containing only NETA is considered, that the systems according to the invention are also, from the point of view of the yields, quite superior to the single product currently containing a progestogen, the product ESTRAGEST® TTS. There are thus obtained, respectively, relative to ESTRAGEST® TTS, a yield 38-fold and 39-fold higher for Examples 8 and 9. The previous conclusion for oestradiol (Table IV) is again valid for NETA.

In conclusion, all the results given above demonstrate the undeniable advantages of the transdermal matrix system according to the invention, on different skin models, by tests ex vivo, for the delivery of an oestrogen and/or of a progestogen compared with other devices already marketed.

They show, in particular, that the specific formulation of the invention, which combines with an SIS copolymer the pair propylene glycol laurate/N-alkyl-2-pyrrolidone and a VA/VP copolymer, makes it possible to carry out the delivery of an oestrogen component/progestogen component combination by a matrix system and to obtain, for the delivery of one or more hormones, yields which appear to be exceptional.

TABLE I

Tests on male "nude" mouse abdominal skin

|      |          | Ex 1  | Ex 2  | Ex 3 | Ex 4  | ESTRAGEST ® TTS |
|------|----------|-------|-------|------|-------|-----------------|
| Es   | $Q_0$    | 51.2  | 47.2  | 43.3 | 55.1  | 1570            |
|      | $Q_{24}$ | 8.64  | 10.6  | 11.5 | 14.4  | 3.1             |
|      | Y        | 16.9  | 22.4  | 26.6 | 26.1  | 0.2             |
| NETA | $Q_0$    | 197   | 287.4 | 248  | 212.6 | 4790            |
|      | $Q_{24}$ | 12.5  | 13.9  | 27.1 | 22.3  | 8.2             |
|      | Y        | 6.3   | 5     | 11   | 10.5  | 0.17            |

$Q_0$: initial quantity of Es or NETA expressed in μg/cm²
$Q_{24}$: quantity of Es or NETA liberated over 24 hours expressed in μg/cm²
Y: yield expressed as a percentage (Y = 100.$Q_{24}$/$Q_0$)

TABLE II

Tests on pig ear skin

|      |          | Ex 1  | Ex 2   | Ex 3  | Ex 4  | ESTRAGEST ® TTS |
|------|----------|-------|--------|-------|-------|-----------------|
| Es   | $Q_0$    | 45.7  | 57.5   | 42.5  | 53.1  | 1570            |
|      | $Q_{48}$ | 23.5  | 22.44  | 20.36 | 21.6  | 9.66            |
|      | Y        | 51.5  | 39     | 47.9  | 40.6  | 0.61            |
| NETA | $Q_0$    | 184.2 | 345.3  | 252.4 | 212.6 | 4790            |
|      | $Q_{48}$ | 24.4  | 35.9   | 36.6  | 21.4  | 42.6            |
|      | Y        | 13.2  | 10.4   | 14.5  | 10    | 0.9             |

$Q_0$: initial quantity of Es or NETA expressed in $\mu g/cm^2$
$Q_{48}$: quantity of Es or NETA liberated over 48 hours expressed in $\mu g/cm^2$
Y: yield expressed as a percentage (Y = $100.Q_{48}/Q_0$)

TABLE III

Tests on human skin ex vivo

|      |          | Ex 3  | Ex 5  | ESTRAGEST ® TTS |
|------|----------|-------|-------|-----------------|
| Es   | $Q_0$    | 42.5  | 37.4  | 1570            |
|      | $Q_{48}$ | 32.4  | 34.5  | 10.02           |
|      | Y        | 76.3  | 92.2  | 0.64            |
| NETA | $Q_0$    | 255.1 | 150   | 4790            |
|      | $Q_{48}$ | 90.5  | 66.2  | 16.85           |
|      | Y        | 35.5  | 44.1  | 0.35            |

$Q_0$: initial quantity of Es or NETA expressed in $\mu g/cm^2$
$Q_{48}$: quantity of Es or NETA liberated over 48 hours expressed $\mu g/cm^2$
Y: yield expressed as a percentage (Y = $100.Q_{48}/Q_O$)

TABLE IV

Tests on male "nude" mouse abdominal skin

|          | Ex 6  | Ex 7  | OESCLIM ® |
|----------|-------|-------|-----------|
| $Q_0$    | 101.2 | 102.4 | 1570      |
| $Q_{24}$ | 25.6  | 29.3  | 14.2      |
| Y        | 25.3  | 28.7  | 3.1       |

$Q_0$: initial quantity of Es expressed in $\mu g/cm^2$
$Q_{24}$: quantity of Es liberated over 24 hours expressed in $\mu g/cm^2$
Y: expressed as a percentage, that is to say (Y = $100.Q_{24}/Q_0$)

TABLE V

Tests on male "nude" mouse abdominal skin

|      |          | Ex 8  | Ex 9 | ESTRAGEST ® TTS |
|------|----------|-------|------|-----------------|
| NETA | $Q_0$    | 452.7 | 350  | 4790            |
|      | $Q_{24}$ | 29.5  | 23   | 8.2             |
|      | Y        | 6.5   | 6.6  | 0.17            |

$Q_0$: initial quantity of NETA expressed in $\mu g/cm^2$
$Q_{24}$: quantity of NETA liberated over 24 hours expressed in $\mu g/cm^2$
Y: yield expressed as a percentage, that is to say (Y = $100.Q_{24}/Q_0$)

We claim:

1. A transdermal matrix system for the percutaneous administration of at least one hormone, said matrix system having a support and an adhesive matrix wherein said matrix comprises:

(a) 20 to 50 parts by weight of a poly(styrene-isoprene-styrene) triblock (SIS) copolymer, (b) 30 to 60 parts by weight of a tackifying resin, (c) 4 to 25 parts by weight of propylene glycol laurate, (d) 2 to 10 parts by weight of an N-alkyl-2-pyrrolidone compound in which the alkyl group is a $C_4$—$C_{15}$ group, (e) 0.1 to 2 parts by weight of a stabilizing agent, (f) 0.1 to 12 parts by weight of at least one hormone selected from the group consisting of oestrogen compounds and progestogen compounds, and (g) 1 to 12 parts by weight of a vinyl acetate/N-vinyl-2-pyrrolidone (VA/VP) copolymer.

2. The transdermal matrix system according to claim 1 wherein the N-alkyl-2-pyrrolidone compound is N-octyl-2-pyrrolidone.

3. The transdermal matrix system according to claim 2 wherein the vinyl acetate/N-vinyl-2-pyrrolidone copolymer has a vinyl acetate content of between 30 and 70% by weight relative to the weight of the said copolymer.

4. The transdermal matrix system according to claim 1 wherein the poly(styrene-isoprene-styrene) triblock copolymer has a styrene content of between 14 and 50% by weight relative to the weight of said copolymer.

5. The transdermal matrix system according to claim 1 wherein the poly(styrene-isoprene-styrene) triblock copolymer has a styrene content of between 17 and 47% by weight relative to the weight of said copolymer.

6. The transdermal matrix system according to claim 1 wherein the hormone is an oestrogen compound.

7. The transdermal matrix system according to claim 6 wherein said oestrogen compound is 17β-oestradiol.

8. The transdermal matrix system according to claim 1 wherein the hormone is a progestogen compound.

9. The transdermal matrix system according to claim 8 wherein said progestrogen compound is norethisterone acetate.

10. The transdermal matrix system according to claim 1 wherein the matrix contains a mixture of an oestrogen compound and a progestogen compound.

11. The transdermal matrix system according to claim 10 wherein said oestrogen compound is 17β-oestradiol and said progestrogen compound is norethisterone acetate.

12. A method for preparing a transdermal matrix system according to claim 1 said method comprising the steps of:

(α) introducing, with stirring, into a reactor containing a solvent for an SIS copolymer, at a temperature below the boiling temperature of said solvent, at least one hormone selected from the group consisting of oestrogen compounds and progestogen compounds, a stabilizing agent, a VA/VP copolymer, an N-alkyl-2-pyrrolidone compound and propylene glycol laurate and then homogenizing the resulting mixture, (β) incorporating into the mixture thus obtained an SIS copolymer and a tackifying resin and stirring, still at the same temperature, until complete dissolution of the constituents and complete homogenization of the mixture;

(γ) coating the homogeneous mixture thus obtained, at room temperature, onto a temporary anti-adherent support so as to obtain a coating of 50 to 300 g/m² on the said support; and, (δ) evaporating the solvent by heating said coating at a temperature greater than the boiling point of said solvent, and then transferring said coating onto a permanent support.

13. A method for preparing a transdermal matrix system according to claim 1, said method comprising the steps of:

(α) mixing an SIS copolymer, a stabilizing agent and a tackifying resin at a temperature greater than 110° C. and then homogenizing the resulting mixture;

(β) incorporating into the homogeneous mixture thus obtained propylene glycol laurate, an N-alkyl-2-pyrrolidone compound and a VA/VP copolymer, at a temperature of between 80 and 110° C., and the homogenizing the resulting mixture;

(γ) incorporating into the homogeneous mixture thus obtained at least one hormone selected from the group consisting of oestrogen compounds and progestogen compounds, and then homogenizing the resulting mixture;

(δ) coating the homogeneous mixture thus obtained, at a temperature of between 80 and 130° C., onto a temporary anti-adherent support so as to obtain a coating of 50 to 300 g/m² on the said support; and, (ε) transferring said coating onto a permanent support.

14. A method for the treatment of menopause symptoms comprising applying to the skin of a patient in need of such a treatment a transdermal matrix system according to claim 1 which contains a therapeutically effective amount of at least one hormone selected from the group consisting of oestrogen compounds and progestrogen compounds.

15. A method for the treatment of osteoporosis symptoms comprising applying to the skin of a patient in need of such a treatment a transdermal matrix system according to claim 1 which contains a therapeutically effective amount of at least one hormone selected from the group consisting of oestrogen compounds and progestrogen compounds.

16. The transdermal matrix system according to claim 1 wherein the matrix comprises, for a total of 100 parts by weight:

(a) 31.3 parts by weight of SIS copolymer, (b) 44 parts by weight of tackifying resin, (c) 10.5 parts by weight of propylene glycol laurate, (d) 4 parts by weight of N-octyl-2-pyrrolidone, (e) 0.2 part by weight of a stabilizing agent, (f) 4 parts by weight of norethisterone acetate, and (g) 6 parts by weight of a vinyl acetate/N-vinyl-2-pyrrolidone (VA/VP) copolymer.

17. The transdermal matrix system according to claim 1 wherein the matrix comprises, for a total of 100 parts by weight:

(a) 37.8 parts by weight of SIS copolymer, (b) 38 parts by weight of a tackifying resin, (c) 15 parts by weight of propylene glycol laurate.

(d) 4 parts by weight of N-octyl-2-pyrrolidone, (e) 0.2 part by weight of a stabilizing agent, (f) 1 part by weight of 17β-oestradiol, and (g) 4 parts by weight of a vinyl acetate/N-vinyl-2-pyrrolidone (VA/VP) copolymer.

18. The transdermal matrix system according to claim 1 wherein the matrix compsirse, for a total of 100 parts by weight:

(a) 34.3 parts by weight of SIS copolymer, (b) 41 parts by weight of a tackifying resin, (c) 14 parts by weight of propylene glycol laurate, (d) 4 parts by weight of N-octyl-2-pyrrolidone, (e) 0.2 part by weight of a stabilizing agent, ($f_1$) 0.5 part by weight of 17β-oestradio, ($f_2$) 3 parts by weight of norethisterone acetate, and (g) 3 parts by weight of a vinyl acetate/N-vinyl-2-pyrrolidone (VA/VP) copolymer.

* * * * *